US011603527B2

(12) United States Patent
Smith

(10) Patent No.: US 11,603,527 B2
(45) Date of Patent: Mar. 14, 2023

(54) METHOD AND KIT FOR VIRAL VECTOR ISOLATION

(71) Applicant: Global Life Sciences Solutions USA LLC, Marlborough, MA (US)

(72) Inventor: Trevor Smith, Marlborough, MA (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 413 days.

(21) Appl. No.: 15/855,162

(22) Filed: Dec. 27, 2017

(65) Prior Publication Data

US 2019/0194642 A1   Jun. 27, 2019

(51) Int. Cl.
| | |
|---|---|
| *C12N 5/00* | (2006.01) |
| *C12N 15/10* | (2006.01) |
| *C07K 14/725* | (2006.01) |
| *C12N 15/86* | (2006.01) |
| *C12N 5/0783* | (2010.01) |
| *B01D 15/38* | (2006.01) |
| *C12N 7/00* | (2006.01) |
| *C12M 1/00* | (2006.01) |
| *C12M 3/00* | (2006.01) |

(52) U.S. Cl.
CPC ....... *C12N 15/101* (2013.01); *B01D 15/3809* (2013.01); *C07K 14/7051* (2013.01); *C12M 23/42* (2013.01); *C12M 47/02* (2013.01); *C12N 5/0636* (2013.01); *C12N 7/00* (2013.01); *C12N 15/86* (2013.01); *C12N 2510/00* (2013.01); *C12N 2740/13051* (2013.01); *C12N 2740/15043* (2013.01); *C12N 2740/15051* (2013.01); *C12N 2740/15052* (2013.01); *C12N 2740/16051* (2013.01)

(58) Field of Classification Search
CPC ...... C12N 15/101; C12N 5/0636; C12N 7/00; C12N 15/86; C12N 2510/00; C12N 2740/13051; C12N 2740/15043; C12N 2740/15051; C12N 2740/15052; C12N 2740/16051; B01D 15/3809; C07K 14/7051; C12M 23/42; C12M 47/02
See application file for complete search history.

(56) References Cited

U.S. PATENT DOCUMENTS

| | | | | |
|---|---|---|---|---|
| 2004/0106184 | A1* | 6/2004 | Senesac | C12N 7/00 |
| | | | | 435/239 |
| 2010/0231504 | A1* | 9/2010 | Bloem | G06F 3/013 |
| | | | | 345/156 |
| 2011/0258837 | A1* | 10/2011 | Scannon | B23P 25/00 |
| | | | | 29/592 |
| 2014/0323695 | A1* | 10/2014 | Takeda | C07K 16/065 |
| | | | | 530/351 |
| 2014/0323698 | A1* | 10/2014 | Duthe | B01D 15/3809 |
| | | | | 530/387.3 |
| 2015/0064768 | A1 | 3/2015 | Kapre | |
| 2015/0175950 | A1 | 6/2015 | Hirschel et al. | |
| 2015/0329640 | A1* | 11/2015 | Finer | C12N 5/0636 |
| | | | | 424/93.21 |

FOREIGN PATENT DOCUMENTS

| | | | |
|---|---|---|---|
| JP | 2000510682 A | 8/2000 | |
| JP | 2001506126 A | 5/2001 | |
| JP | 2013538556 A | 10/2013 | |
| WO | 96/27677 A2 | 9/1996 | |
| WO | 9826048 A1 | 6/1998 | |
| WO | WO 2001/048155 * | 7/2001 | ............... C12N 7/00 |
| WO | WO 2003/039459 A2 * | 5/2003 | |
| WO | WO-2003039459 A2 * | 5/2003 | |
| WO | 2012010280 A1 | 1/2012 | |
| WO | WO 2013/154928 A1 * | 10/2013 | |
| WO | WO-2013154928 A1 * | 10/2013 | ............... C12N 7/00 |

OTHER PUBLICATIONS

Burova et al. Chromatographic purification of recombinant adenoviral and adeno-associated viral vectors: methods and implications, Gene Therapy (2005) 12, S5-S17.*
Levine et al., Mol Ther. Meth. Clin. Dev., vol. 4, 2017, pp. 92-101 (Year: 2017).*
PCT International Search Report and Written Opinion for PCT Application No. PCT/EP2018/086202 dated Feb. 19, 2019 (14 pages).
Levine et al., "Global Manufacturing of CAR T Cell Therapy," Molecular Therapy, 2017, 4:92-101.
Office Action Issued in Japanese Patent Application No. 2020-536056, dated Oct. 3, 2022 with English Summary (14 pages).
Vicente, et al., "Analysis of Adsorption of a Baculovirus Bioreaction Bulk on an Ion-Exchange Surface by Surface Plasmon Resonance," Journal of Biotechnology, 148, pp. 171-181, 2010.

* cited by examiner

*Primary Examiner* — Catherine S Hibbert
(74) *Attorney, Agent, or Firm* — Eversheds Sutherland (US) LLP

(57) ABSTRACT

The present invention relates to a method for purification of viral vectors, more closely it relates to purification of viral vectors from producer cells by using a single automated process. The method comprises the following steps: a) adding producer cells and cell lysis buffer to a processing container; b) mixing said producer cells and cell lysis buffer in said processing container to obtain a mixture; c) flowing said mixture through a chromatography column for purification of viral vectors, wherein the viral vectors are adsorbed on said chromatography column; and d) eluting viral vectors from the chromatography column into a product container.

14 Claims, 6 Drawing Sheets

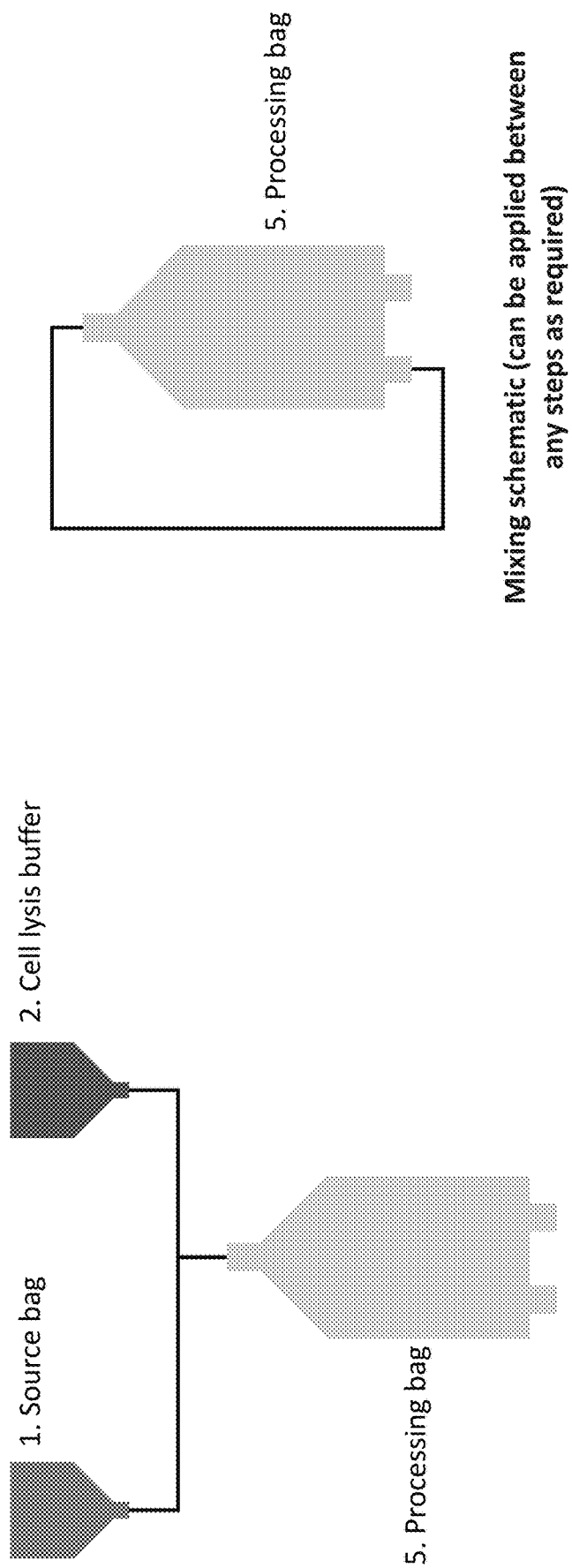

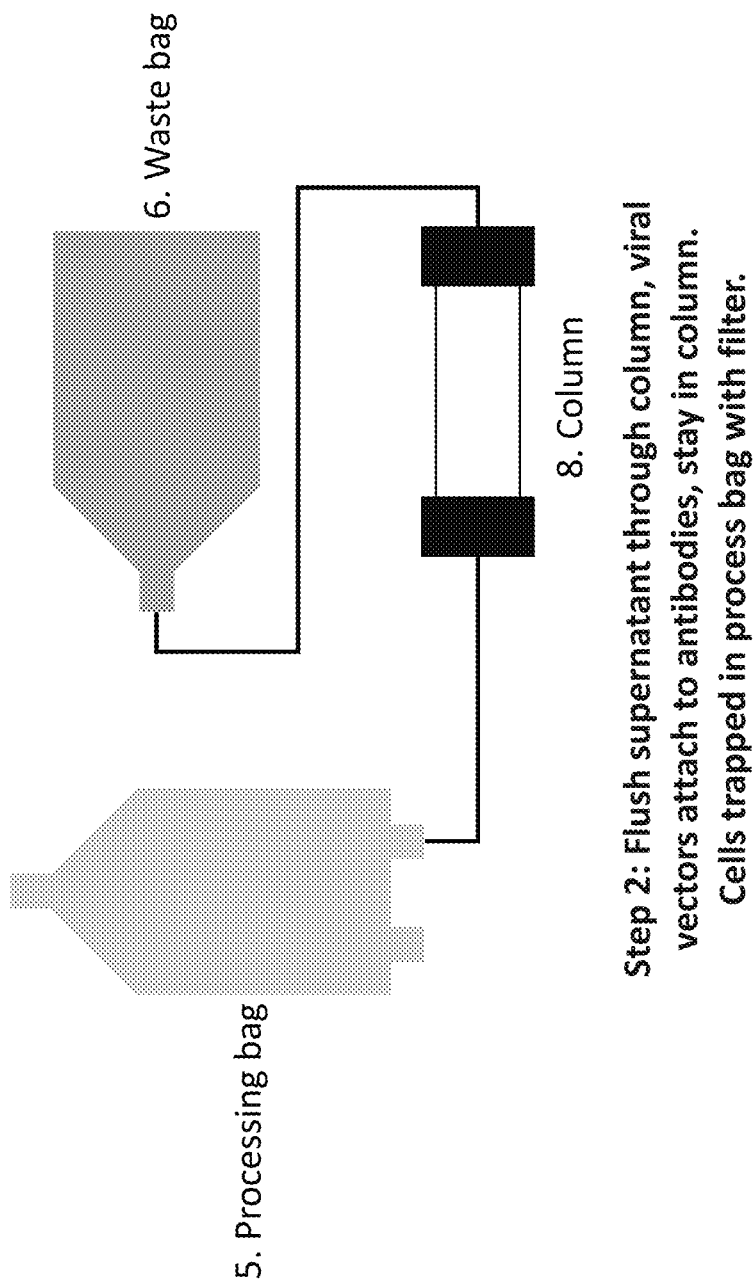

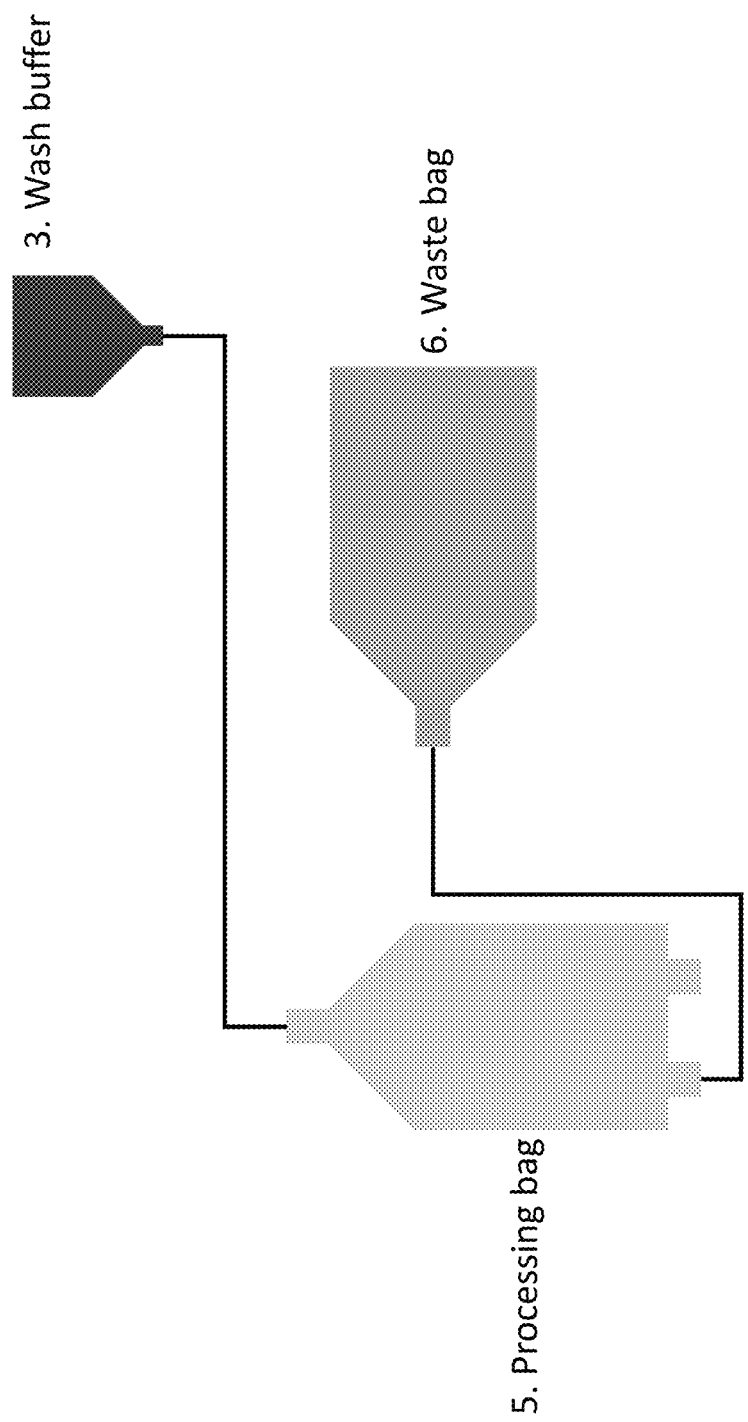

METHOD AND KIT FOR VIRAL VECTOR ISOLATION

FIELD OF THE INVENTION

The present invention relates to purification of viral vectors, more closely it relates to a method and kit for purification of viral vectors from producer cells by using a single automated process.

BACKGROUND OF THE INVENTION

Cell therapy is a newly emerging area for treatment of severe diseases, such as cancer, and represents an addition to conventional therapies. For decades, cancer treatment has been restricted to chemotherapy, and radiation therapy. More recently, biological drugs like imatinib (Gleevec®) and trastuzumab (Herceptin®) have been increasingly common. These drugs target cancer cells by horning in on specific molecular changes seen primarily in those cells.

But over the past several years a new form of therapy, cell therapy or immunotherapy, has emerged as an option for, for example, cancer treatment.

A rapidly emerging immunotherapy approach is called adoptive cell transfer (ACT): collecting and using patients' own immune cells to treat their cancer. There are several types of ACT (TILs, TCRs, and CARs), but the one that is closest, to producing a treatment approved by the Food and Drug Administration (FDA) is called CAR T-cell therapy.

Until recently, the use of CAR T-cell therapy has been restricted to small clinical trials, largely in patients with advanced blood cancers. But these treatments have nevertheless captured the attention of researchers and the public alike because of the remarkable responses they have produced in some patients—both children and adults—for whom all other treatments had stopped working.

One CAR T-cell therapy was approved in August 2017 for the treatment of children with acute lymphoblastic leukemia (ALL). And a second, for adults with advanced lymphomas, obtained approval in October 2017.

CAR T-cell therapy relies on the T cells, which have a critical role in orchestrating the immune response and killing cells infected by pathogens. The therapy requires drawing blood from patients and separating out the T cells. Next, using a viral vector, the T cells are genetically engineered to produce receptors on their surface called chimeric antigen receptors, or CARs.

Currently, the purification of viral vectors for cellular transformation is not an automated process.

Viral vector purification typically requires a column to isolate particles reliably. For example, lentivirus purification requires antibodies with specificity to their protein coat. As in the case of cellular isolation, each type of viral strain requires antibody specific purification approaches. However, separation of viral particles from cells and cellular debris could also be accomplished through centrifugation steps using density gradients or similar solution-based technologies.

Contaminants in this step, as with many other biological processes, could at best delay treatments to the patient and at worst negatively impact their health. The creation of a trustworthy, "set-and-forget" process would ensure safety and efficacy of downstream processes.

It would be highly desirable to be able to automate the process of generating a purified viral vector for transformation of T cells into CAR T cells. This is especially relevant in the current cell therapy market, as lentiviral vectors are the most commonly used strategies for gene insertion into T cells for CAR expression.

Hitherto there is no such desired purification method available that is broadly applicable to the scores of viral strains capable of transforming cells.

Thus, there is still a need of a broadly applicable method for purification of viral vectors.

SUMMARY OF THE INVENTION

The present invention avoids the drawbacks within prior art by providing a broadly applicable method and kit for purification of viral vectors in an automated process, preferably using an instrument, such as the Xuri Cell Harvester®, already intended to be included in the cell therapy workflow.

Using a combination of solution based cell lysis, column extraction of viral particles, washing, and elution steps, the method is adoptable to purification of any type of viral vectors in an all-in-one kit product which offers several advantages compared to prior art. The method and kit of the invention provide a closed, aseptic system for purification of viral vectors in an automated process.

In a first aspect the invention relates to a method for isolation of viral vectors comprising a gene of interest following production by cultivation of said viral vectors in producer cells, comprising the following steps in a continuous workflow: a) adding producer cells and cell lysis buffer to a processing container; b) mixing said producer cells and cell lysis buffer in said processing container to form a mixture; c) flowing said mixture through a chromatography column comprising affinity resin for purification of viral vectors, wherein the viral vectors are adsorbed on said resin in said chromatography column; and d) eluting viral vectors from the resin in the chromatography column into a product container.

The viral vectors obtained in step d) in product container are used to transfect fresh producer cells which then are cultivated before the steps a)-d) are repeated at least once, such as 3-6 times or passages.

The production scale, i.e. the amount of number of viral vectors obtained from the method, is directed by the saturation point of the affinity resin and volume of the chromatography column. The column volume in the preferred configuration is up to 200 mL.

Optionally the method comprises the following step after step c) or d): releasing wash buffer into the processing container to flush out cells/debris and eject it into a waste container.

Preferably the processing container, product container and chromatography column are mounted in one and the same cassette, and wherein the cell lysis buffer, the wash buffer, elution buffer and optionally waste container are located outside the cassette. All parts 1-8, including the cassette are sometimes referred to as a viral vector kit in the present invention. Preferably the containers are plastic bag containers. The producer cells may be provided in a source bag or any other suitable container. The containers may be plastic bags or any other suitable containers. The cassette is mounted on a device with pumps that facilitate the flow of liquid through the kit as described in below in FIGS. 2-7. Pinch valves allow specific lines to be selected for the different inputs, and allows the culture to be processed centrally in the processing container.

The method and kit of the invention is used with an instrument, preferably the Xuri Cell Harvester®, which has a digital interface that allows the user to set specific process parameters to optimize their own workflow. While the cassette enables automatization of traditional viral vector isolation with an affinity column, the method also involves releasing viral particles using the cell lysis buffer, as well as employing specific viral binding with antibodies, ligands, or other anchorable molecules in the same process. The method and kit can also be intermediately employed to purify extant viral cultures, making its versatility quite novel in the field of viral vector production.

The chromatography column is an interchangeable affinity column specific for a chosen viral vector. Affinity columns can include, but are not limited to, antibodies, ligands, or any other anchorable molecules specific for binding viral vectors within the column.

In one embodiment, the processing container is provided with an exit port completed with a filter to retain any intact cells/cellular debris within the processing container.

The viral vectors may be any virus, such as lentivirus or gamma retrovirus.

Preferably the gene of interest comprises a disease-regulating gene, such as a gene encoding a chimeric antigen (CAR).

The purity of the isolated viral vectors in product container may be tested in a quality assay involving SPR (surface plasmon resonance) detection before repeating steps a)-d). In this assay affinity ligands of the same type as in the affinity column may be immobilized to a sensor surface.

In a second aspect, the invention relates to use of viral vectors isolated according to the invention for cell therapy, such as for transformation of T cells into CAR T cells.

In a third aspect, the invention relates to a kit comprising a processing container, a product container and a chromatography column mounted in one and the same cassette, and further comprising a source container for producer cells, a cell lysis buffer, a wash buffer, an elution buffer and optionally a waste container located outside the cassette. All containers are preferably plastic bag containers.

BRIEF DESCRIPTION OF THE DRAWINGS

FIG. 2 shows the first step (lysing of producer cells) in utilizing the viral vector isolation kit.

FIG. 3 shows a mixing step which can be applied between any steps in utilizing the kit as required.

FIG. 4 shows the second step (flush supernatant through column) in utilizing the viral vector isolation kit.

FIG. 5 shows the third step (process bag washing) in utilizing the viral vector isolation kit.

DETAILED DESCRIPTION OF THE INVENTION

With the advent of multiple FDA-approved CAR T-cell therapies, the most effective candidate viruses are known, such as lentivirus and gamma retroviruses.

The present inventors are providing a platform for purification of any viral vectors in a small to medium scale, comprising a system of bags and chromatography column, wherein the platform is limited only by the saturation point and volume of the resin in the chromatography column, and wherein the column is interchangeable to allow purification of different types of viral vectors.

The present invention will be described more closely in relation to the accompanying drawings.

The invention will be described with lentivirus as preferred viral vector but any viral vectors may be purified on the platform of the invention.

The components of the kit according to the invention comprises a source bag, containing producer cells previously infected with lentivirus, and any lentivirus in the supernatant that had been produced in culture. Furthermore, cell lysis buffer to lyse the producer cells, releasing additional viral particles thus maximizing yield. A wash buffer is used to rinse the kit of cellular debris before the final column elution. Finally, a column elution solution is required to release the purified viral particles into the final product bag.

Figure 1:
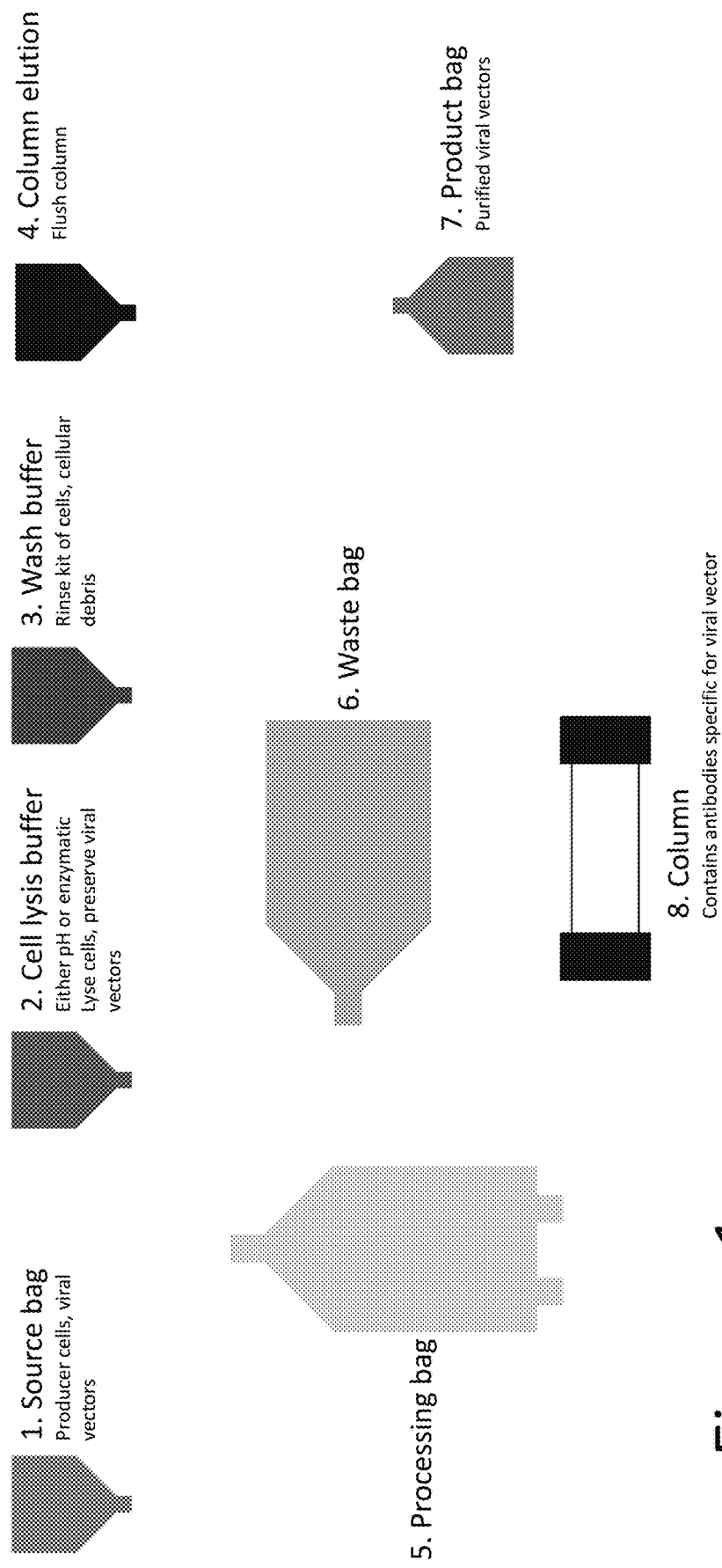
FIG. 1 is a schematic view showing the different components of the viral vector isolation kit used in a method according to the invention.

FIG. 1 shows the different components of the viral vector isolation kit. The kit comprises eight parts or containers, preferably seven bag-type containers and one column-shaped container.

First there is a source container, preferably a source bag, comprising producer cells 1 producing viral vectors. The volume of this bag is scalable, limited only by the saturation point of the chromatography column.

Cell lysis buffer 2 is provided in a cell lysis buffer container or bag for cell lysis of the producer cells from the source bag, wherein the lysis action is mediated by pH or enzymatically. The cell lysis buffer will lyse the cells but preserve the viral vectors. The lysis buffer 2 will contain a highly concentrated lysing agent in a small volume for ease of use and flexibility for the variable volumes seen in the source bag. Examples of cell lysis buffer are typically detergent based, to disrupt the lipid bilayer cell membrane. Cellular lysis buffer must be aggressive enough to lyse the cells, but not interfere with the antibody binding or protein interactions in the downstream columnar isolation. It is important that the cell lysis buffer is highly concentrated so that it's final concentration when mixed with the producer cell suspension is appropriate.

Wash buffer 3 is preferably provided in a bag and comprises wash buffer to rinse kit of cells, cellular debris. The volume will be in sufficient enough quantities to remove all traces of lysis buffer 2.

Elution buffer 4 is preferably provided in a column elution buffer bag comprising an elution buffer for flushing column 8. The volume should be large enough to allow for multiple elution steps from the column to maximize viral yield.

Container 5 is a processing container or bag and should be about 0.5-1 L, such as 850 mL, which corresponds to the volume of the processing bag in the Xuri Cell Harvester® Processing Kit.

Container 6 is a waste container or bag and should be similar in volume to the processing bag in the current Xuri Cell Harvester® Processing Kit, up to 6 L.

Container or bag 7 is a product bag for the purified viral vectors. The volume should be sufficient enough to hold the entire elution buffer 4 volume.

Column 8 is a chromatography column packed with chromatography media or resin provided with antibodies or ligands specific for the desired viral vector to be isolated.

The column 8 is interchangeable using any technology, for example GE Healthcare "ReadyMate"® connector systems.

Figure 6:
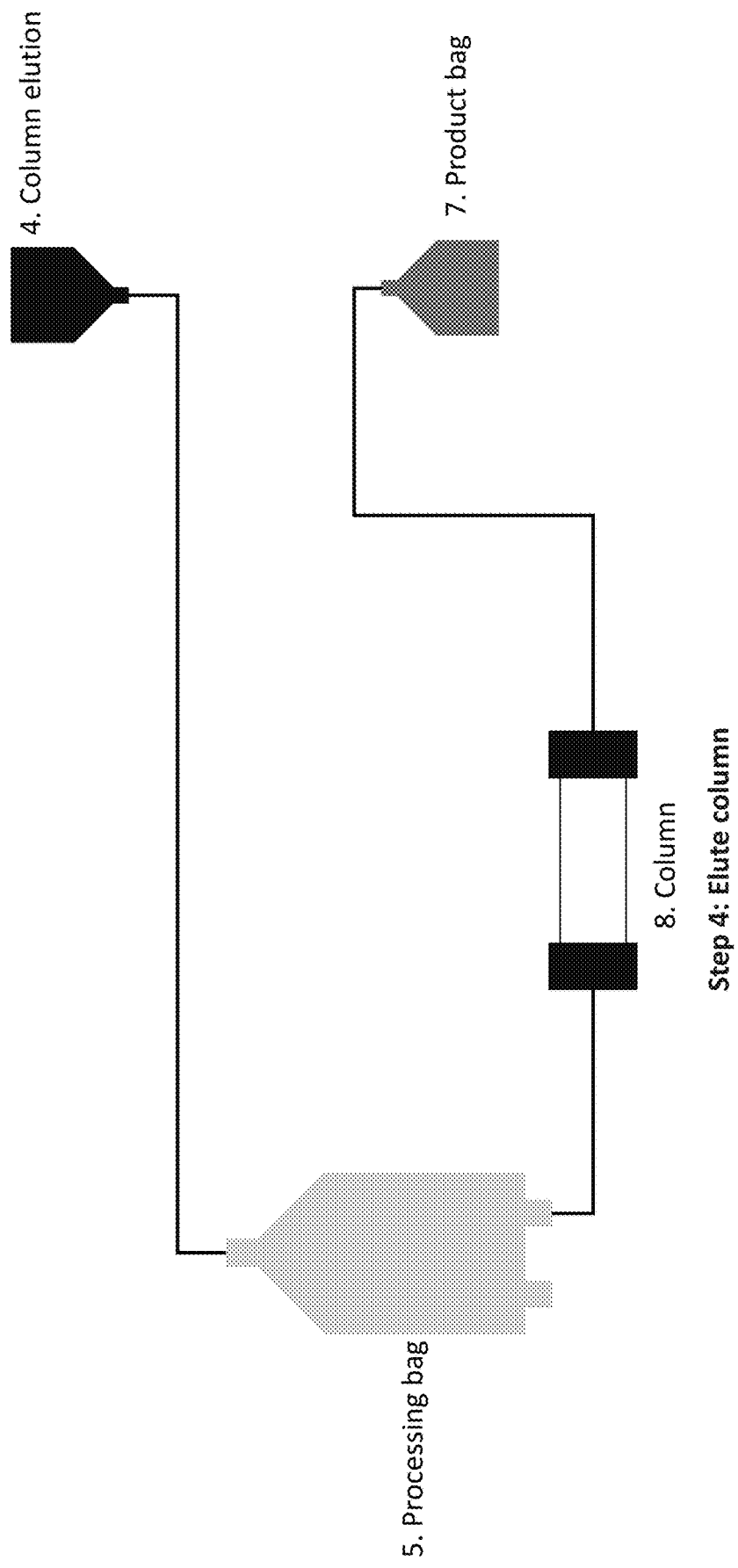
FIG. 6 shows the fourth step (column elution) in utilizing the viral vector isolation kit.

As shown in FIG. 2, in the first step of the process, producer cells 1 and cell lysis buffer 2 are added to the processing bag 5. The cells and buffer are circulated through the kit as shown in FIG. 3 to ensure mixing and subsequent lysis occurred. With the cells lysed, the mixture is pushed through the column 8 as shown in FIG. 4. The exit port for this step would be completed with a filter that kept any intact cells/cellular debris within the processing bag 5. To ensure all cells/debris was flushed out of the system, the wash buffer 3 would be released into the processing bag 5, circulated through the system, and finally ejected into the waste bag 6 as shown in FIG. 5. Following this, the elution buffer for the column 8 is released, pushing the viral vectors into the final product bag 7 as shown in FIG. 6.

Figure 7:
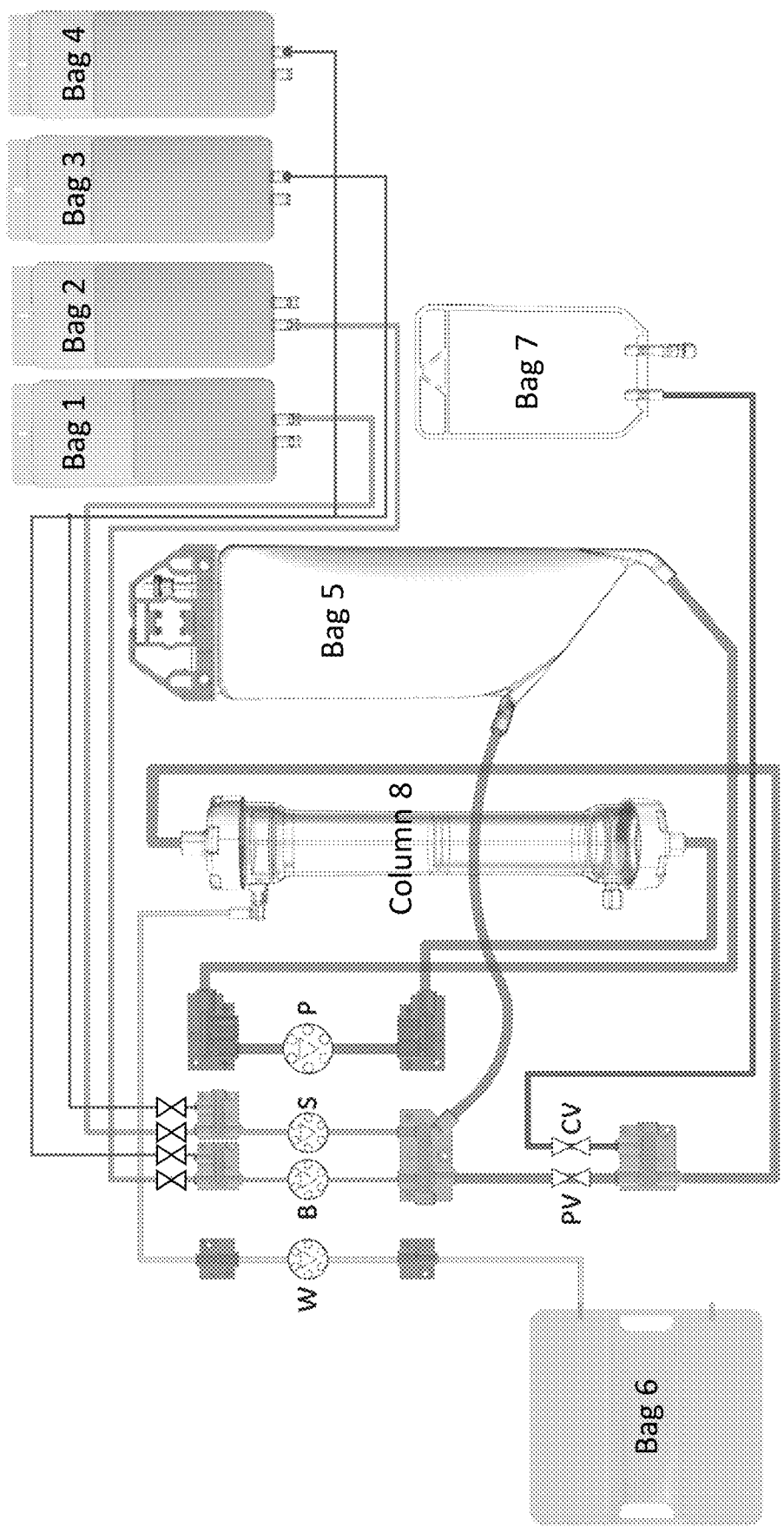
FIG. 7 is a more detailed view of the fluid paths of the viral vector isolation kit used in the present invention.

FIG. 7 is a more detailed view of the viral isolation kit use in the method of the invention. Valves, in this case pinch valves, are denoted by the triangular hourglass symbols, and pump heads are denoted by the circles with six rollers. All components of the kit except for the input components (1-4) and waste bag (6) are mounted to a cassette. The cassette preferably will be mounted within the Xuri Cell Harvester® described in WO2017/109071 (incorporated herein by reference), preferably by a rail mechanism.

The instrument for use with the viral vector kit according to the present invention is the same as described in WO2017/109071. In operation, the instrument includes mechanical elements including pumps, pinch valves and weighing mechanisms, which are reusable, together with the removeable and disposable low cost viral vector kit which comprises all the fluid elements (e.g. fluid paths, buffer bags and column) necessary for viral vector harvesting. The combination of these features results in a method for viral vector isolation wherein a selected viral vector kit is readily mounted on the instrument. No mechanical parts of the instrument encounter fluids, which means that cleaning of the mechanical parts between different viral vector isolation runs is not required. This is especially important for subsequent use in cellular therapeutic applications where the readily achievable aseptic operating conditions of the instrument provide a much-improved chance of therapeutic success, as well as reduced costs and turn-around times.

The viral vector isolation kit has several similarities with the fluid path schematic from the Xuri Cell Harvester® Processing Kit described in WO2017/109071 but there are several additions. Namely, bags for wash buffer and elution buffer must be added to accommodate the wash buffer and elution solution for the process. Lines connecting these bags to the main circulation of the kit were also added, feeding into pinch valves and junction pieces that would select which input bag could flow through the system without having to add pump heads currently installed in the Xuri Cell Harvester®. The chromatography column (8) would replace the typical location of the hollow fiber filter cartridge.

EXAMPLE

A specific example of the viral vector isolation procedure of the invention fitting into a CAR T-cell therapy workflow, consists of the traditional static culture of human embryonic kidney 293T (HEK 293T) cells transfected with lentiviral plasmids coding viral machinery such as gag/pol, rev, an envelope gene, and a transfer plasmid encoding the gene of interest, in this case the chimeric antigen receptor (CAR). After approximately 72 hours, when the viral load within the cell culture media has reached a suitable concentration, the culture of producer cells is transported from the static culture to a source container, which could be a source bag that could be welded or luer connected to the cassette. This is different from prior art, as traditional workflows typically require the user to transfer only the supernatant to harvest viral particles. According to the invention, both the producer cells and the supernatant are used for harvest. The other input bags, the cell lysis buffer, the wash buffer, and the column elution buffer, are connected in a similar manner. The user then selects the column with specific affinity for the viral vectors to be harvested, and sterile connects it to the cassette with disposable aseptic connectors like the ReadyMate™ system. When all of the components are attached, the cassette is inserted into the Xuri Cell Harvester® instrument and the protocol is selected.

To begin, the source bag containing the producer cells and viral vectors is added to the processing bag. Once empty, the cell lysis buffer is added to the processing bag. The fluid of the processing bag is then mixed by pushing it through a circuit within the cassette. This step is optional, depending on the desired workflow. The processing bag then empties into the chromatography column, where the anchored, viral-specific ligands bind the virus, and cellular debris is passed through to the waste bag. When the processing bag volume is fully passed through the column, the column elution buffer then enters the cassette, passes through the processing bag towards the column, and elutes the viral particles into the final product bag.

The product is then introduced to an extant T-cell culture to transform the T-cells to CAR T-cells. Alternatively, the product can be re-suspended with a fresh culture of producer cells to transfect the cells with a purified product and cultivate the producer cells with the intention being to generate a more refined product, as defective viruses would have been discarded out of the column. This is in-line with cGMP processes that require multiple purification steps. Once the viral vectors are deemed pure and stable enough as judged by a quality assay, a new viral vector isolation kit could be employed to isolate the vectors once or several times more for use in transforming T-cells.

Current methodology calls for harvesting the viral supernatant, a process that only involves removing the media from the HEK-293T cell culture. Viral particles still within the cells are left behind at this step. The supernatant is then clarified using depth filtration and ultra-filtered with a hollow fiber filter cartridge. The viral vector-specific column (8) is chosen to have an affinity for viral particles significant enough to reduce this process to one step. This combined with the lysing of cells provides a higher viral yield when compared to current processes.

The invention claimed is:

1. A method for isolation of viral vectors comprising a gene of interest following production by cultivation of said viral vectors in producer cells, comprising the following steps in a continuous workflow with an instrument: a) adding a culture of producer cells and a cell lysis buffer to a processing container; b) mixing said culture of producer cells and said cell lysis buffer in said processing container to form a mixture and allowing the culture of producer cells to lyse; c) flowing said mixture comprising debris of said lysed culture of producer cells, residual cells, and said cell lysis buffer from the processing container through a chromatography column comprising affinity resin for purification of viral vectors, wherein the viral vectors are adsorbed on said resin in said chromatography column; d) eluting viral vectors from the resin in the chromatography column into a product container, wherein the processing container, the product container, and the chromatography column are mounted in a removable cassette on the instrument, wherein the cell lysis buffer, a wash buffer, and an elution buffer are located outside the cassette in respective lysis buffer, wash buffer, and elution buffer bags on the instrument, wherein the eluting the viral vectors from the resin comprises flowing the elution buffer from the elution buffer bag outside the cassette through the chromatography column in the cassette, and wherein, after step c) or d) the wash buffer is released from the wash buffer bag outside the cassette into the processing container inside the cassette to flush out cells/debris and eject it into a waste container.

2. Method according to claim 1, further comprising following step d) transfecting fresh producer cells with the eluted viral vectors; cultivating the transfected cells; and repeating steps a)-d) with the cultivated and transfected cells at least once.

3. Method according to claim 1, wherein the viral vectors eluted from the method are directed by the volume and saturation point of the resin in the chromatography column.

4. Method according to claim 1, wherein the waste container is located outside the cassette.

5. Method according to claim 1, wherein the chromatography column is interchangeable with another chromatography column in the cassette and comprises affinity resin specific for a chosen viral vector.

6. Method according to claim 1, wherein the processing container is provided with an exit port completed with a filter to retain any intact cells/cellular debris within the processing container.

7. Method according to claim 1, wherein the viral vectors are lentivirus or gamma retrovirus.

8. Method according to claim 1, wherein the gene of interest comprises a disease-regulating gene.

9. Method according to claim 2, further comprising the intermediate step of testing the purity of the eluted viral vectors in the product container in a quality assay involving SPR (surface plasmon resonance) detection before transfecting the fresh producer cells and repeating steps a)-d).

10. A method of cell therapy treatment in a patient in need thereof, comprising administering to the patient a treatment effective amount of viral vectors, the method further comprises isolating the viral vectors by a method comprising the following steps in a continuous workflow with an instrument:
a) adding a culture of producer cells and a cell lysis buffer to a processing container;
b) mixing said culture of producer cells and said cell lysis buffer in said processing container to form a mixture; c) flowing said mixture from the processing container through a chromatography column comprising affinity resin for purification of viral vectors, wherein the viral vectors are adsorbed on said resin in said chromatography column; and
d) eluting viral vectors from the resin in the chromatography column into a product container, wherein the processing container, the product container, and the chromatography column are mounted in a removable cassette on the instrument, wherein the cell lysis buffer, a wash buffer, and an elution buffer are located outside the cassette on the instrument, wherein the eluting the viral vectors from the resin comprises flowing the elution buffer from outside the cassette through the chromatography column in the cassette, and wherein the viral vectors are used for transformation of T cells into CAR T cells.

11. A kit comprising a processing container, a product container and a chromatography column each mounted in a single cassette, the kit further comprising a source container for producer cells, a cell lysis buffer, a wash buffer, and an elution buffer each located outside the cassette in respective cell lysis buffer, wash buffer, and elution buffer bags.

12. The kit of claim 11, further comprising a waste container located outside the cassette.

13. The method according to claim 1, wherein the cell lysis buffer does not interfere with antibody binding or protein interactions in the column.

14. The method according to claim 1, wherein the lysis is mediated by pH or enzymatically.

* * * * *